United States Patent [19]

Gabbay

[11] 4,275,469
[45] Jun. 30, 1981

[54] PROSTHETIC HEART VALVE

[75] Inventor: Shlomo Gabbay, Bronx, N.Y.

[73] Assignee: Shelhigh Inc., New York, N.Y.

[21] Appl. No.: 103,214

[22] Filed: Dec. 13, 1979

[51] Int. Cl.³ .............................................. A61F 1/22
[52] U.S. Cl. ............................................................ 3/1.5
[58] Field of Search ........................................ 3/1.5, 1

[56] References Cited

U.S. PATENT DOCUMENTS

| | | | |
|---|---|---|---|
| 15,192 | 6/1856 | Peale | 3/1.5 X |
| 2,832,078 | 4/1958 | Williams | 3/1.5 X |
| 3,445,916 | 5/1969 | Schulte | 3/1.5 X |
| 3,608,097 | 9/1971 | Bellhouse et al. | 3/1.5 X |
| 3,736,598 | 6/1973 | Bellhouse et al. | 3/1.5 |
| 3,739,402 | 6/1973 | Cooley et al. | 3/1.5 |
| 3,755,823 | 9/1973 | Hancock | 3/1.5 |
| 4,218,782 | 8/1980 | Rygg | 3/1.5 |

FOREIGN PATENT DOCUMENTS 2355959  6/1975  Fed. Rep. of Germany ............... 3/1.5

OTHER PUBLICATIONS

"Heart Valve Replacement with Autologous Fascia Lata", by M. I. Ionescu et al., The Journal of Thoracic & Cardiovascular Surgery, vol. 60, No. 3, Sep. 1970, pp. 331-354.
"Comparative Study of Cardiac and Vascular Implants in Relation to Thrombosis", by C. A. Hufnagel et al., Surgery, vol. 61, No. 1, Jan. 1967, pp. 11-16.
"Fixation of Aortic Valve Homografts with Metal Rings", by A. S. Geha et al., The Journal of Thoracic & Cardiovascular Surgery, vol. 54, No. 5, Nov. 1967, pp. 605-615 & 628-629.
"Heart Valve Replacement with Reinforced Aortic Heterografts", by G. H. Wooler et al., The Journal of Thoracic & Cardiovascular Surgery, vol. 56, No. 3, Sep. 1968, pp. 333-350.
"Mitral & Aortic Valve Replacement with Fascia Lata on a Frame", by W. S. Edwards et al., The Journal of Thoracic & Cardiovascular Surgery, vol. 58, No. 6, Dec. 1969, pp. 854-858.

Primary Examiner—Ronald L. Frinks
Attorney, Agent, or Firm—Bierman & Bierman

[57] ABSTRACT

A prosthetic heart valve consists of a tubular membrane having a flexible generally circular inlet end adapted to be attached to the annulus of a heart with one side of the tube held to the heart cavity as by attachment to the papillary muscle while the other side of the tube is formed as an extended single flap adapted to move toward and away from the membrane on the attached side to provide a closed or open valve at the outlet end.

18 Claims, 8 Drawing Figures

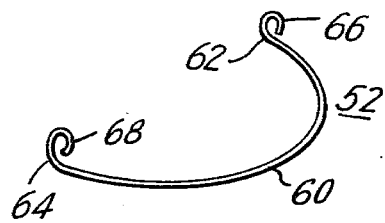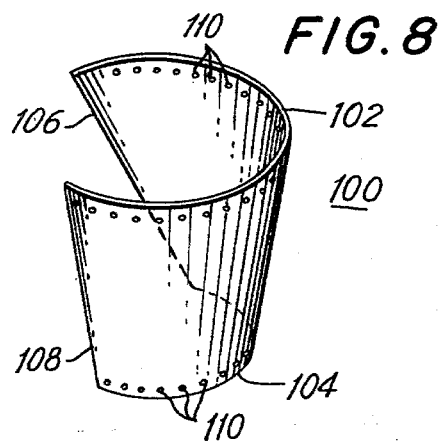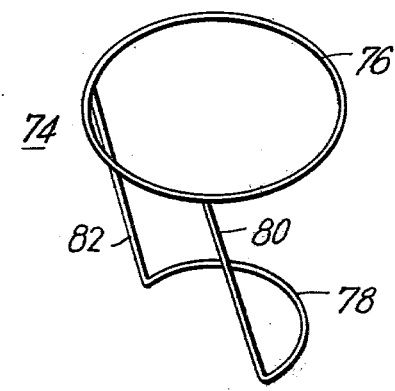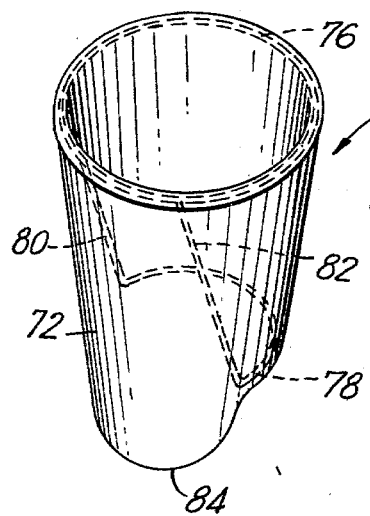

PROSTHETIC HEART VALVE

BACKGROUND OF THE INVENTION

1. Field of Application

This invention relates to valves for the human heart and more particularly to a prosthetic heart valve.

2. Description of the Prior Art

In the field of heart valves there have been many attempts to produce a valve that is similar or substantially similar to the natural heart valve. The reason is that if the replacement valve differs in any substantial way from the natural valve, its reaction in the heart muscle might be so detrimental as to cause failure of the heart itself. One approach is known as the Starr-Edwards valve. It utilizes vertical struts, a steel or plastic ball movably entrapped in cage and having a larger diameter than the opening in a circular ring. The pressure of blood flowing through the ring moves the ball away from the ring and permits blood flow through the valve. The reversal of pressure causes the ball to be seated again against the ring to block flow through the valve. There are many problems with the Starr-Edwards type valve. The flow is not axial since it must flow around the ball. Such a flow quite often creates a very serious problem since it tends to cause turbulence (eddy currents) which restricts the flow of blood and may cause blood clots. The presence of blood clots in turn leads to thromboembolisms and improper seating of the valve, and anticoagulants must be used continually. The projecting cage member can cause scarring of the heart wall; the clicking sound of the valve can be emotionally disturbing.

There has been some work done in attempting to produce a valve which more closely simulates the shape and axial flow characteristics of the natural heart valve, and, of course, eliminates the ball. Most of these have been directed to tricuspid or three lip valves.

Tricuspid valves may require the use of certain heart valves from swine. One of the problems encountered is that hundreds of pigs have to be slaughtered before one or two perfect valves can be found. Secondly, in a tricuspid valve, as will be explained hereinafter, if there is slight damage or shrinkage to one of the cusps, the valve does not close properly. Also, swine valves are not particularly large and because of mounting problems, only about 30% of the area of the mounting ring can be used for the opening in the valve. Thus, much of the internal diameter of the normal heart valve is lost with this type of valve.

Moreover, tricuspid valves have an inherent problem in that the three lips must close in exact alignment or the valve does not properly close. If one lip is slightly out of line or misshapen, the other two lips cannot make up for the difference and, therefore, leakage occurs. Likewise, after the valve has been used for some period of time, one of the cusps may become slightly inflexible and immobile, causing tissue to build up on that cusp and further reduce its mobility. The result is stenosis or total lack of movement of the cusp. This reduces the size of the opening and the amount of blood flowing through the valve. Also, the stenosis may cause turbulence in the flow of blood and improper closure which almost invariably leads to failure of the valve. Some more of the problems and description of many types of heart valves are discussed in detail in the Journal of Thoracic and Cardiovascular Surgery, Vol. 68, No. 3, September, 1974, pages 261 to 269 and by applicant in Vol. 76, No. 6, December, 1978, pages 771 to 787.

There has been some effort to produce a two cusp valve which attempts to simulate the shape and flow of the natural heart valve. However, the principal problems with such a valve (as shown in U.S. Pat. No. 3,739,402 to Cooley et al.) are the lack of an adequate volume of blood flow through the valve and the inability to obtain complete closure.

This patent specifies that the lips can only open to approximately 2 millimeters, or only open to a small fraction (20%) of the valve passage area. Thus, only 20% of the amount of blood entering the valve can exit and the result is a tremendous strain on the heart and the valve, which may possibly lead to failure of both. Reduction in flow also causes high back pressure within the heart and may seriously damage the inside of the heart.

The inflexibility of the lips of the device disclosed in the Cooley et al. patent causes them to close along a thin narrow line at their leading edge. This closing creates two serious problems. With a narrow line of closure, the slightest deformity in either lip prevents complete closing and causes leakage through the valve. Second, since the valve closes only along this narrow line, the valve is often unable to remain closed when subjected to the extreme pressures in the heart. This is especially important when the valve is used in the mitral position in the heart, since the pressure differential across the valve in that position is substantial, and any leakage could lead to cardiac failure.

A heart valve is needed which closely simulates the natural heart valve by having the flexibility to open to substantially the same size as the natural opening and the flexibility to completely close and to remain closed against the force of large pressure differentials.

In my copending U.S. application, Ser. No. 841,791, filed Oct. 13, 1977, I have disclosed an improved two cusp heart valve with a semiflexible support ring and two lips which closely simulates a natural heart valve. Still, it would be beneficial to more closely simulate a natural heart valve by providing a more flexible support.

It is, therefore, an object of this invention to provide a prosthetic heart valve which closely resembles the natural heart valve.

It is a further object of this invention to provide a heart valve having full axial laminar flow through a tubular member.

A still further object of this invention is to provide a heart valve having sufficient flexibility to open to the full diameter of the valve and to fully close and remain completely closed.

Another object of this invention is to provide a heart valve which moves in conjunction with the annulus of the opening in which it is placed.

Still another object of this invention is to provide a heart valve which is strong enough to resist the pressure of the heart without failure.

Yet still another object of this invention is to provide a heart valve having proper closure and minimal resistance to flow.

Another object of this invention is to provide a heart valve with a single movable lip.

To the above ends, I have provided a prosthetic valve for the heart comprising a tubular membrane having an inlet opening at one end adapted to attach the valve to the annulus of a heart and an outlet opening at a second end. A support structure is adapted to attach the membrane to the heart for preventing the second end from protruding through the inlet opening when the valve closes.

BRIEF DESCRIPTION OF THE DRAWINGS

FIG. 5 is an illustration of the support element of the present invention;

FIG. 6 illustrates a second embodiment of the present invention;

FIG. 7 is an illustration of the support structure in the second embodiment; and FIG. 8 is an illustration of a still further embodiment of a support structure.

Figure 1:
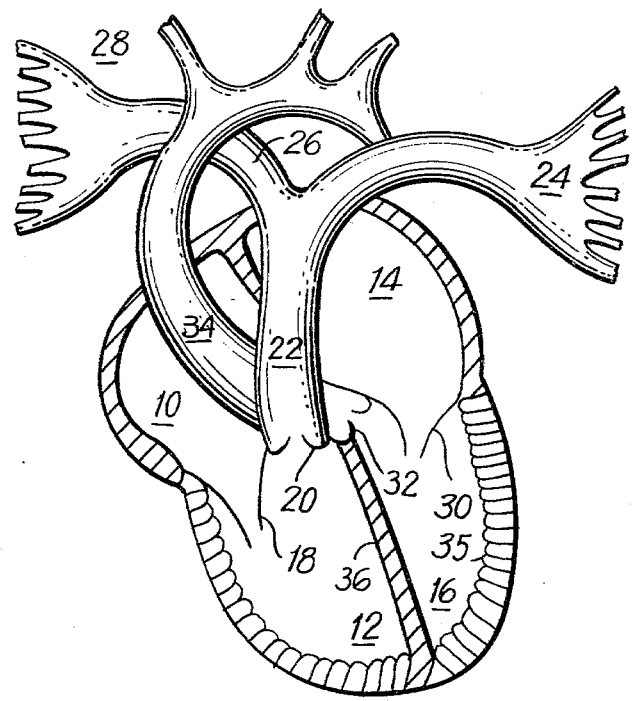
FIG. 1 is a schematic cross section view of a human heart.

The manner in which the valve according to the present invention operates can best be understood by reference to FIG. 1 diagrammatically illustrating the anatomy of the human heart. As there shown, there are four basic chambers, the right atrium 10, the right ventricle 12, the left atrium 14 and the left ventricle 16. Normally, blood flows into the heart from the superior vena cava (not shown) into the right atrium 10, through tricuspid valve 18 and into right ventricle 12. It continues through pulmonary valve 20, pulmonary trunk 22, right and left pulmonary arteries 24 and 26, and finally into the lungs 28. From lungs 28 the blood comes back through left atrium 14, mitral valve 30, left ventricle 16, aortic valve 32, aorta 34 and thence through the rest of the body. The two most important valves are mitral valve 30 and aortic valve 32. The basic reason is that left ventricle 16 is the basic pumping part of the heart. The walls 35 and 36 of left ventricle 16 are much thicker and more muscular than anywhere else in the heart. The pressures in left ventricle 16 range from 0-5 and 90-180 m.m. Hg., whereas in the other parts of the heart, such as right ventricle 12, they range between 0-5 and 2-30 m.m. Hg. When blood flows from left atrium 14 to left ventricle 16, mitral valve 30 opens and aortic valve 32 closes. Next, left ventricle 16 contracts with mitral valve 30 closing. Then, aortic valve 32 opens allowing blood to flow into aorta 34. If mitral valve 30 leaks oxygenated blood into left atrium 14, a reduction of blood flowing through aorta 34 may be caused and substantially less oxygenated blood reaches the rest of the body. Additionally, leakage through aortic valve 32 causes an increase in the size of the heart muscle which may eventually lead to cardiac failure. Thus, even slight leakage in mitral valve 30 or aortic valve 32 causes blood to flow in the wrong direction through the heart and may result in the eventual death of the person involved.

There are many reasons for failure of heart valves. Some of the most common are rheumatic diseases, such as rheumatic fever and congenital defects, such as birth defects.

In these diseases, the cusp of one of the valves becomes stiff and may either be permanently open or permanently closed and unable to function. Substantial leakage occurs and may eventually result in death. This leakage is often referred to as heart murmur because of the sound of the flow of blood through the valve in the wrong direction.

Figure 2:
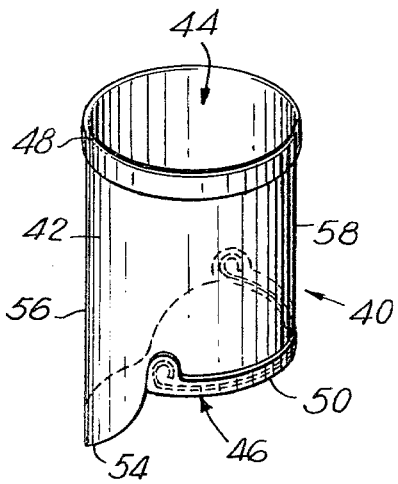
FIG. 2 illustrates a prosthetic heart valve according to the present invention.

When a mitral valve 30 becomes defective, it may be replaced by prosthetic valve 40 according to the present invention, as hereinafter described with reference to FIG. 2.

The valve 40 is primarily constructed of a tubular membrane 42 having substantially the same diameter throughout. More specifically, the cross-sectional area of the opening throughout the tubular membrane 42 from the inlet 44 to the outlet opening 46 is substantially the same. Therefore, blood readily flows through valve 40 without any significant loss of pressure. As such, there is no substantial impediment and a minimal amount of friction to the passage of blood. Since the outlet 46 and the inlet 44 are substantially equal, they differ from those prior art valves in which the outlet area was less than the inlet area. In those valves, due to this difference in area, a venturi effect was created causing a substantial amount of frictional resistance to the flow of blood and a substantial drop in the flow rate. This puts pressure on the heart and may eventually lead to its failure. In the present valve, that pressure differential is substantially eliminated.

The end of the tubular membrane forming inlet 44 may be made by folding over a portion of the membrane 42 as at 48, i.e., by doubling the thickness so that the end will have the additional strength required to hold the sutures which are sewn in to connect the membrane to the annulus of the heart, as will be further described. The amount of material folded down may be relatively small and it is within the scope of the present invention to eliminate this fold if desired.

The outlet end 46 of the membrane includes a first portion 50 which is attached to the support structure or stent 52, shown in more detail in FIG. 5. More specifically, this section may be folded over to cover the support structure and prevent the latter from contacting the blood or heart wall. Although it is not absolutely necessary to provide this fold of material about the support structure, it provides an additional advantage of strengthening the membrane near the support structure at the location where sutures connect the support structure and the membrane to the wall of the heart, as will be further described.

A second portion 54 at the outlet end of the membrane preferably extends below the first portion 50 and thereby provides a free flap of material depending from one side 56 thereof. At its end, this flap is preferably but not necessarily semicircular in shape. This additional material is provided to increase the surface area of the side 56 in order to provide better closure of the valve as will be described. Although this is the preferable embodiment, it is within the scope of the present invention to form the sides 56 and 58 of a uniform length, the side 56, however, being in the form of a free unsupported flap. In addition, the flap 54 may also be folded up along its bottom.

The membrane is made of a biological material such as dura mater (the membrane surrounding the human brain). The dura mater is taken from cadavers and processed so that it is totally inert and thus not be subject to rejection by the human body. This material is extremely strong and flexible and has a high modulus of elasticity so that the valve can be continuously opened and closed with the membrane still retaining its original configuration. Other biologically acceptable materials, such as animal pericardium with gluteraldehyde and dura mater of animals such as pigs, sheep and calves treated by gluteraldehyde may be used. Gluteraldehyde is useful because the cross linking increases the strength of the dura mater. Also gluteraldehyde is an antiseptic and sterilizes the material before use.

While the membrane forming the valve of the present invention has been illustrated as a continuous tubular structure, it is obvious that the tube can be formed of two half-tubes sewn longitudinally together along their adjoining sides. In this case, the juncture line preferably would rise vertically from the free ends 62 and 64 of the stent 52.

The support structure 52 (FIG. 5), which may be made of high-grade surgical steel, includes a curved element 60, which is formed with substantially the same radius as the tubular membrane and preferably is long enough to extend around slightly more than half of the circumference of the membrane. At its ends, the curved element 60 has two upward projecting struts 62 and 64 bent over at its ends as at 66 and 68. The ends of the struts may have other configurations, such as, for example, triangular, circular, semicircular, square, rectangular, or any other desired shape. The important consideration in forming the struts is to make them high enough to support the membrane when the valve closes and low enough to prevent their touching and interfering with the inlet opening of the valve.

The support structure 52 is preferably formed from a unitary length of wire stock which may be any suitable strong material, such as, for example, a high-grade surgical steel like "Eligiloy." This material must be both strong and flexible. Generally, it is not necessary to cover the support structure with any other material, since it is covered with the membrane. However, it is within the scope of the present invention to cover it with any desired material, such as, for example, plastic like a medical grade silicone.

The manner in which the prosthetic valve according to the present invention is utilized will now be described with reference to FIGS. 2 and 3.

It is attached after removal of the defective valve by sewing (stitches 60) the inlet end 48 of the valve on to the remaining tissue around the circumference or annulus of the natural valve.

The outlet end 50 of the valve is held in position by means of one or more sutures 62 which may be stitched around the covered curved element 52 and connected to the papillary muscle 64 to hold the valve in place, as will be further described. If desired, the sutures 62 may be connected to any suitable part of the heart, such as, for example, by running the sutures 62 through the wall 35 of the heart and sewing the ends through a plaget or fabric or in any other desired manner.

Figure 3:
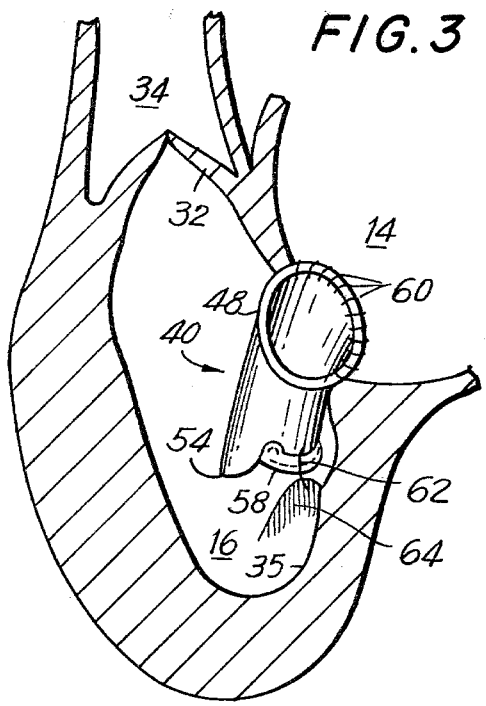
FIG. 3 is a schematic view of the left ventricle of a human heart with a prosthetic valve of this invention implanted therein.

With the valve in place, as shown in FIG. 3, blood from the left atrium 11 can easily flow into the left ventricle 16 through the inlet opening 44 of the valve 40. Since the opening of the valve is formed of an extremely thin membrane material which is merely folded down at 48, the flow can be substantially the same as through a normal mitral valve. This aspect of the invention is very important because the amount of flow area affects the amount of activity in which an individual may engage.

Figure 4:
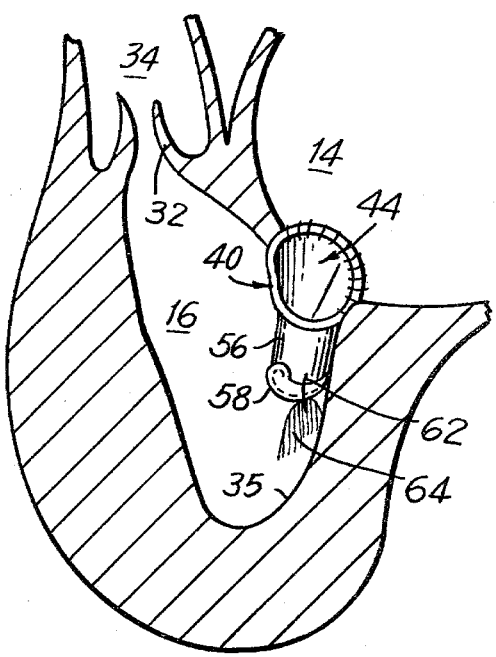
FIG. 4 is a view similar to that of FIG. 3 with the left ventricle in the contracted position.

Referring to FIG. 4, the heart is illustrated with a left ventricle 16 in a somewhat contracted pumping position with the aortic valve 32 in open position and the artificial valve 40 (replacing the mitral valve) in a closed position. The end of the valve has become smaller because the annulus of the heart surrounding the inlet opening 44 is a sphincter muscle which closes approximately 30%. The contraction of the ventricle 16 forces the blood against the side 56 and moves the material forming this wall and more particularly flap 54 against the inner wall of the side 58, whereby the valve 40 is closed and blood located in the left ventricle cannot pass back through the valve to the left atrium 14. When the pressure within the left ventricle builds to a high enough level, the aortic valve 32 opens and the blood is pumped into the aorta 34 and on to the rest of the body as previously explained.

A number of significant advantages are achieved with the prosthetic valve of the present invention. Since the inlet opening 44 of the tubular membrane 42 is completely flexible, there is no impedance to the restriction of the mitral valve opening as was present in prior prosthetic heart valves. Therefore, there is a significant reduction in the many complications caused by prior art prosthetic heart valves. Due to the flexibility of the inlet opening 44, the heart can open and close in a normal manner without any restrictions created by the implanted valve. The stitches 60 are not under strain as in valves with rings having a less flexible annulus where the stitches were subjected to a strain when the mitral annulus opened and closed. This advantage substantially reduces the chance for tearing and leakage across the valve perimeter. Also, in the past, it was dangerous to use a large valve because of the difficulty in contracting the big valve during the pumping of the heart. With the present invention, it is feasible to use a large valve which may provide an orifice area which is substantially the same size as that orifice area of the natural valve being replaced. Since the flow area through the membrane is substantially equal throughout the present valve, turbulence is minimized and the bloos flows without any significant loss of pressure. Thus, a primary cause of blood coagulation is eliminated and avoids the need to give the patient anticoagulants for the remainder of his or her life as with many prior heart valves. In addition, the flow area through the valve is substantially equal from the inlet to the outlet and the two factors together virtually eliminate any excess pressure on the heart which might eventually lead to its failure.

The flap 54 on the first side 56 is preferably slightly longer than the second side 58. When the valve 40 closes, this flap provides more closure area and provides an extra safety precaution that the valve does not leak. Since the present valve has only a single flap, even if it were to shrink slightly or become stiff, the valve will still tightly close. The length and diameter of the valve 40 may be sized according to the heart in which it is to be placed. One important limitation is that the support structure 52 is joined to the heart so that it does not contact the inlet opening 44 and interfere with the closing of the heart valve. Further, the support structure must be long enough (usually either half or slightly more than half the circumference of the tubular membrane 42), so that the first side 56 is not able to protrude through or even contact the inlet opening 44 and thereby interfere with the closing of the inlet opening or the opening and closing of the valve itself.

The prosthetic valve as disclosed may also be used to replace other valves such as the aortic valve 32. In this event, the inlet opening 44 would be sewn in at the annulus left from the removed, damaged, original aortic valve and the outlet portion would extend into the aorta 34 where it would be fastened.

A second embodiment of the present invention, as seen in FIGS. 6 and 7, provides a prosthetic heart valve 70 with a tubular membrane 72 substantially the same as in the first embodiment. The major difference lies in the support member 74 which is placed within the tubular membrane as will be described, and forms a firmer supporting structure.

The support member 74 may be formed from a single piece of material with the inlet end 76 formed as a complete circle. The outlet end 78 if preferably a semicircle and may vary from 40 to 70% of a circle. The vertical struts 80 and 82 of the support structure are preferably parallel to each other and at an obtuse angle with respect to the two ends. The support structure may be constructed of any desired strong but highly flexible material, such as, for example, a synthetic material like polypropylene, Delrin or Teflon, or metal.

The membrane 72 similar to the type described in the first embodiment is placed over the support structure 74 and may be folded at each end so as to completely encase the support structure within the membrane which is sutured thereto about ends 76 and 78 and struts 80 and 82. As provided in the first embodiment, the nonsupported side of the membrane may have an extended flap 84 adjacent the outlet opening for providing extra security when the valve closes. As in the form of invention shown in FIGS. 2-5, the membrane may be made of two pieces which in the present case would be sewn together along the line of the struts 80, 82.

The completed valve may be installed in place of a mitral, aortic or tricuspid valve of the heart as in the first embodiment. The completed valve with the support structure 74 may be affixed to the mitral annulus by sewing about the inlet end. Several sutures may affix the outlet end to the papillary muscle of the heart or through the wall thereof as previously explained.

In operation, the valve performs in a similar manner to the first embodiment in that when the annulus of the mitral valve contracts, the flexible support structure also easily adapts itself to such contraction. Also, the nonsupported side of the membrane, and more particulary flap 84, is readily moved by the blood against the opposite facing wall of the membrane which is supported by the support structure 74 to close the valve. This structure, at the same time, prevents the flap from protruding into the tubular configuration and interfering with the inlet opening.

A modified form of stent or support 100 is illustrated in FIG. 8. In place of an open framework, the stent is made of solid structure of highly flexible material, preferably a synthetic such as polypropylene, Delrin or Teflon, or even of thin metal in the form of a tube open at opposite ends and along one side. The upper end 102 preferably extends about two thirds of the circumference while the lower end 104 about one half of the circumference with slanting edges 106 and 108 interconnecting the same, the resulting stent thus having the general shape of the open frame of FIG. 7. THe tubuler membrane such as 72 in FIG. 6 is placed over support 100, the latter being provided with a series of openings 110 at top and bottom for attaching the membrane thereto. The resulting valve will be substantially identical in outward appearance to that shown in FIG. 6 and will be attached to the heart annulus at the top and to the heart wall at the bottom in the manner previously described.

While specific embodiments of the invention have been described, it will be appreciated that the invention is not limited thereto as many modifications thereof may be made by one skilled in the art, which fall within the true spirit and scope of the invention. In addition, while there have been shown the preferred forms of my invention, it should be understood that such modifications may be made without departing from the spirit as comprehended by the following claims.

I claim:

1. A prosthetic heart valve comprising a tubular membrane having an inlet end and an outlet end, the inlet end being adapted to be attached about the annulus of the heart, and a substantially seimcircular supporting structure attached to a semicircular section of the outlet end of said tubular membrane and adapted to be attached to the wall of the heart, whereby the remaining section of the tubular membrane at the outlet end remains free and is movable toward and away from the supported portion thereof to close or open the outlet end of the tubular membrane.

2. A prosthetic heart valve according to claim 1, in which the unsupported end of said tubular membrane is of greater length than the supported end.

3. A prosthetic heart valve according to claim 2, in which said unsupported end is formed as a semicircular flap.

4. A prosthetic heart valve according to claim 1, in which the inlet end of said tubular membrane is folded back upon itself to provide a firm support for attachment to the annulus of the heart.

5. A prosthetic heart valve according to claim 1, in which the ends of the semicircular supporting structure are formed with smooth raised ends, and in which the outlet end of the tubular membrane attached to said supporting structure is folded thereover.

6. A prosthetic heart valve according to claim 1, in which the diameter of said semicircular supporting structure is substantially equal to the diameter of the inlet end of said tubular membrane.

7. A prosthetic heart valve according to claim 1, in combination with a flexible ring enclosed by and supporting the inlet end of said tubular membrane, and a pair of upwardly and forwardly extending struts respectively connecting the ends of said semicircular supporting structure to said flexible ring.

8. A prosthetic heart valve according to claim 7, in which the unsupported end of said tubular membrane is of greater length than the supported end.

9. A prosthetic heart valve according to claim 8, in which said unsupported end is formed as a semicircular flap.

10. A prosthetic heart valve according to claim 7, in which the diameter of said flexible ring is substantially equal to the diameter of said semicircular supporting structure.

11. A prosthetic heart valve according to claim 7, in which said ring, said struts and said supporting structure are formed as a unit of flexible material.

12. A prosthetic heart valve according to claim 11, in which said material is wire stock.

13. A prosthetic heart valve according to claim 12, in which said wire stock is surgical steel.

14. A prosthetic heart valve according to claim 11, in which the diameter of said flexible ring is substantially equal to the diameter of said semicircular supporting structure.

15. A prosthetic heart valve comprising a tubular membrane having an inlet end and an outlet end, the inlet end being adapted to be attached about the annulus of the heart, a supporting structure for said membrane comprising a sheet of flexible material having a length substantially equal to the length of said tubular membrane, and positioned within said tubular membrane, said sheet having a circumference at its upper end substantially equal to two thirds of the circumference of the tubular membrane and a circumference at its lower end substantially equal to one half of the circumference of said tubular membrane, and means attaching the inlet and outlet ends of said tubular membrane to the respective corresponding circumferences at the upper and lower ends of said supporting structure, whereby the unattached portion of the outlet end of said tubular membrane is movable toward and away from the attached portion thereof to close or open the outlet end of the tubular membrane.

16. A prosthetic heart valve according to claim 15, in which the unattached portion of the outlet end of said tubular membrane is of greater length than the attached portion thereof.

17. A prosthetic heart valve according to claim 16, in which said unattached end is in the form of a semicircular flap.

18. A prosthetic heart valve according to claim 15, in which the diameters of the upper and lower ends of said supporting structure are substantially equal.

* * * * *

UNITED STATES PATENT AND TRADEMARK OFFICE
CERTIFICATE OF CORRECTION

PATENT NO. : 4,275,469
DATED : June 30, 1981
INVENTOR(S) : Shlomo Gabbay

It is certified that error appears in the above-identified patent and that said Letters Patent are hereby corrected as shown below:

Column 3, line 34, change reference numeral "28" to --26--.

Column 5, line 56, change reference numeral "11" to --14--.

Signed and Sealed this

Second Day of February 1982

[SEAL]

Attest:

Attesting Officer

GERALD J. MOSSINGHOFF

Commissioner of Patents and Trademarks